United States Patent [19]

Suya

[11] Patent Number: 4,838,788
[45] Date of Patent: Jun. 13, 1989

[54] ARTICULATOR FOR MASTERING DENTURE CORRECTING TECHNICS

[76] Inventor: Hajime Suya, 3-20-17 Shimoochiai, Shinjuku-ku, Tokyo, Japan

[21] Appl. No.: 131,328

[22] Filed: Dec. 8, 1987

Related U.S. Application Data

[63] Continuation of Ser. No. 13,048, Feb. 10, 1989, abandoned.

[30] Foreign Application Priority Data

Feb. 13, 1986 [JP] Japan ............................. 61-29756

[51] Int. Cl.⁴ .......................................... A61C 11/00
[52] U.S. Cl. .................................................. 433/32
[58] Field of Search ............... 433/2, 32, 24; 434/263, 434/264

[56] References Cited

U.S. PATENT DOCUMENTS 2,315,748  4/1943  Thompson ........................... 433/35
3,422,536  1/1969  Garson ................................ 434/264

Primary Examiner—Robert Peshock
Attorney, Agent, or Firm—Cushman, Darby & Cushman

[57] ABSTRACT

A dental articulator for mastering denture correcting technics, comprising an alveolar portion made of thermoplastic organic matter for supporting each of the root portions of an artificial denture and a heater disposed within the alveolar portion made of thermoplastic organic matter just beneath and apart from apexes of the root portions of said artificial denture and extended along apexes of root portions.

3 Claims, 3 Drawing Sheets

ARTICULATOR FOR MASTERING DENTURE CORRECTING TECHNICS

This application is a continuation-in-part of U.S. patent application No. 013,048 filed on Feb. 10, 1987 and now abandoned.

This invention concerns a dental articulator that simulates the shape and function of upper and lower jaws and a denture of a patient for enabling a dental operator to confirm a result obtained when the operator performs denture correction in accordance with a plan therefor and for mastering a method of exactly using a denture correcting tool.

Simulated articulators in the prior art used by dental operators for mastering a method of exactly using denture correcting tools have been made by heating an alveolar portion made of wax of an articulator from the outside thereof and, accordingly, it cannot exactly reproduce the actual movement of dentes. Further, it has been difficult to observe the moving state of artificial dentes or the deformed state of an alveolar portion made of wax of the articulator since it is hindered by an external heating means.

The object of this invention is to provide a dental articulator for mastering denture correcting technics capable of simulating the state of the rotational movement of an artificial tooth due to the lateral load applied to the crown of said artificial tooth closely to the state of rotational movement of an actual tooth and capable of easily observing the moving state of the artificial tooth and the deformation state of an alveolar portion made of thermoplastic organic matter.

The foregoing object of this invention can be attained by a dental articulator for mastering denture correcting technics, comprising an artificial denture, an alveolar portion made of thermoplastic organic matter for supporting each of root portions of said artificial denture at one end thereof, a mold for supporting the other end of said alveolar portion made of thermoplastic organic matter, heating means disposed within said alveolar portion made of thermoplastic organic matter just beneath and apart from apexes of said root portions of said artificial denture and extending along apexes of said root portions for heating a part of said alveolar portion made of thermoplastic organic matter beneath said apexes of said root portions so that the state of the rotational movement of an artificial tooth due to the lateral load applied to the crown of said artificial tooth can be simulated extremely close to the state of the rotational movement of an actual tooth, and an energy supply source for supplying heating energy to said heating means.

In the dental articulator for mastering denture correcting technics according to this invention, since a part of an alveolar portion made of thermoplastic organic matter beneath the apexes of root portions is heated, the state of the rotational movement of an artificial tooth due to the lateral load applied to the crown of said artificial tooth can be simulated much closer to the state of the rotational movement of an actual tooth, and since there is no necessity to dispose the heating means to the periphery of the articulator, the moving state of the artificial tooth and the deformation state of the alveolar portion made of thermoplastic organic matter can easily be observed.

This invention will now be described more specifically while referring to the accompanying drawings, wherein FIG. 1 is a perspective view of a conventional articulator for mastering denture correcting technics;

Figure 1:
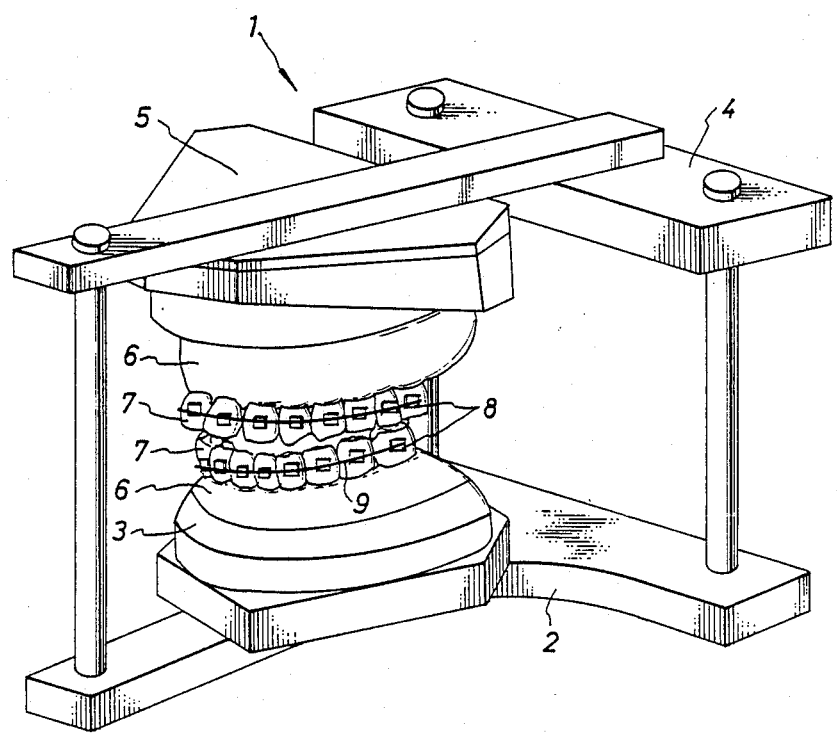

Explanation is at first made to an articulator 1 simulating the shape and function of upper and lower jaws and a denture of a patient as shown in FIG. 1 which has been used so that a dental operator may master a method of exactly using a denture correcting tool. The articulator 1 comprises a lower mold 3 placed on a substrate 2 and an upper mold 5 disposed above a stand 4 by way of an appropriate connecting means capable of simulating the movement of man's jaws. An alveolar portion 6 is secured to each of the lower and upper molds 3, 5 and an artificial denture 7 is inserted into the alveolar portion 6 made of thermoplastic organic material. The artificial denture 7 is attached with brackets 8 and a main arch 9 as a denture correcting tool and the main arch 9 connects each of the brackets 8 bonded to each artificial dent 7.

For using the articulator 1, an extremely fine and elastic metal wire or rubber is at first engaged between appropriate brackets 8 so as to correct the denture 7, to thereby apply an extremely small load to each of the artificial dentes 7, and then the articulator 1 is properly engaged with the metal wire or rubber is immersed in warm water at an appropriate temperature or the articulator 1 is exposed to a warm blow at an appropriate temperature to soften the alveolar portion 6. When the alveolar portion 6 is thus softened, each of the artificial dentes 7 applied with the small load moves in the direction of the load applied. Accordingly, a dental operator can confirm instantly whether the denture can be corrected exactly or not by the correcting method applied by him.

Figure 2:
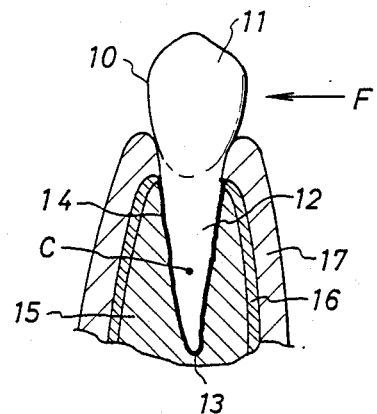
FIG. 2 is a cross-sectional view for a man's dent and a peripheral tissue of dent.

As shown in FIG. 2, a dent 10 is supported by a peripheral tissue of dent on a jaw bone not illustrated in which a crown 11 is exposed to the inside of a mouth and a root 12 is contained within the peripheral tissue which comprises the alveolar bone 14 near the apex of the root 13, sponge bone 15, dense bone 16 and gingiva 17.

If it is assumed that load F is applied laterally to the crown 11, it is generally considered that the dent 10 rotationally moves around a point C as the center, which situates at about ⅓ height from the apex of root 13 along the depth of the root 12.

Figure 3:
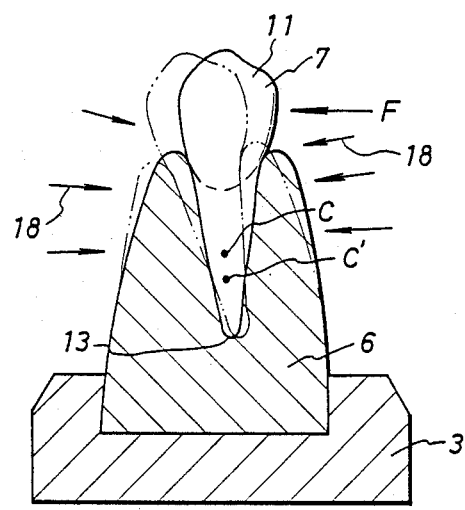
FIG. 3 is a fragmentary cross-sectional view of an articulator in prior art.

However, as shown in FIG. 3, upon softening, the alveolar portion 6, since heat 18 is applied from the outside of the alveolar portion 6 with warm water or warm blow in the conventional articulator 1 as described above, a thinner upper portion softens more as compared with the lower portion in the alveolar portion 6 and, therefore, the center C' for the rotational movement of the artificial dent 7 due to the lateral load F applied to the crown 11 is shifted nearer to the apex of the root 13 than the center point C and the amount of the rotational movement becomes larger (as shown by the chain line in FIG. 3), by which the articulator 1 can not reproduce the actual movement of the dent 10.

Furthermore, it is difficult to confirm the state where the artificial dent 7 is moved or the alveolar portion 6 is deformed, since it is hindered by a warm water vessel filled with warm water or means for generating warm blow.

Figure 4:
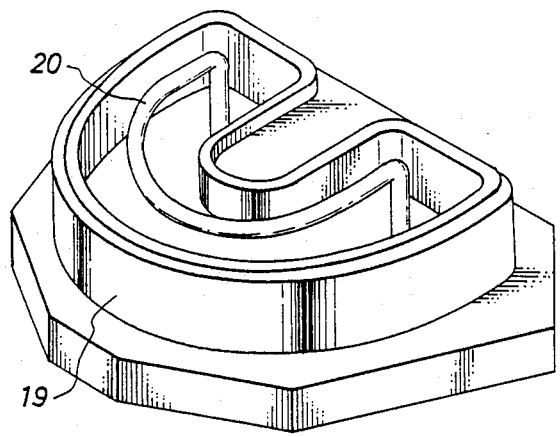
FIG. 4 is a perspective view for a mold used in the articulator according to this invention.
Figure 5:
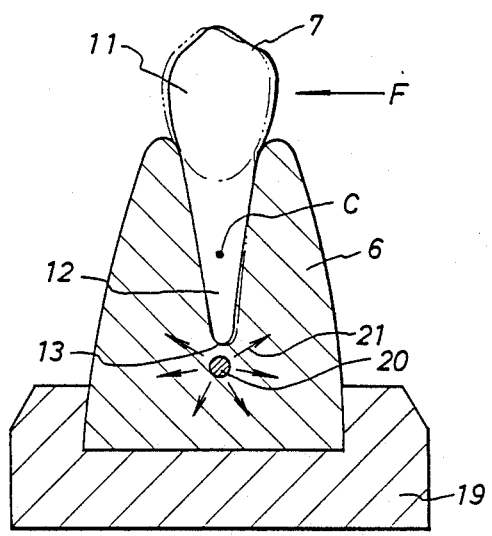
FIG. 5 is a fragmentary cross-sectional view of an articulator according to this invention.

FIG. 4 shows a mold 19 which is similar to the lower or upper mold 3, 5 of the articulator 1 shown in FIG. 1. An electrical resistor 20 preferably applied with insulation is used as heating means in the mold 19, and is disposed above the mold 19 therealong and connected at an appropriate position to an external power source as an energy source not illustrated. Further, the alveolar portion 6 is made of thermo-plastic organic matter, preferably, comprising plastic, wax or paraffin wax so as to contain an electrical resistor 20 therein as shown in FIG. 5, and a denture 7 is formed on the alveolar portion 6 made of thermoplastic organic matter. In this case, it is desirable that the electrical resistor 20 is situated just beneath and apart from apexes of root portions 13 and extending along apexes of said root portions 13, by which heat 21 is applied predominantly to a part of the alveolar portion 6 made of thermoplastic organic matter beneath apexes of the root portions 13 while the strength of the alveolar portion 6 is maintained as it is. Accordingly, the center for the rotational movement of the artificial tooth 7 due to the lateral load F applied to the crown 11 (shown by the chain line in FIG. 5) closely approaches the center C for the rotational movement of an actual tooth. Heating is applied such that the part of the alveolar portion 6 beneath apexes of root portions 13 is heated, preferably, to 20° C.–100° C. Therefore, the state of the rotational movement of an artificial tooth due to the lateral load applied to the crown of said artificial tooth can be simulated extremely closer to the state of the rotational movement of an actual tooth. These molds 19 are used in a state where they are assembled as the articulator 1 as shown in FIG. 1.

In this embodiment, the electrical resistor 20 may be formed in a zig-zag manner or in a vortex shape so as to uniformly heat the alveolar portion 6.

Further, a temperature sensor may, preferably, be disposed to the root 12, so that electrical current to the electrical resistor 20 is controlled by the signal from the sensor, to adjust the heating temperature to the alveolar portion 6.

Furthermore, a tube having an appropriate diameter capable of passing heating warm water therethrough may be used as the heating member.

In addition, the alveolar portion 6 may be constituted by arranging a plurality of thermoplastic organic matters having different softening temperatures in a multi-layered manner so as to favorably move the artificial dent 7 rotationally.

What is claimed is:

1. A dental articulator for mastering denture correcting technics comprising:

an artificial denture comprised of a plurality of artificial teeth each having a root portion;

an alveolar portion made of thermoplastic organic matter for supporting each root portion at one end thereof;

a mold connected to the other end of said alveolar portion for supporting the other end of said alveolar portion;

a resistance wire having a U-shaped portion disposed in the alveolar portion and end portions extending respectively from both ends of said U-shaped portion outside of said alveolar portion, said U-shaped portion embedded within said alveolar portion just beneath and apart from apexes of said root portions of said artificial denture and being out of contact with said artificial denture and extending along said apexes of said root portions, said resistance wire being adapted to heat a part of said alveolar portion beneath said apexes of said root portions by means of only said U-shaped portion when said resistance wire is connected to an electric power supply source.

2. A dental articulator as defined in claim 1, wherein said resistance wire is formed in a zigzag shape.

3. A dental articulator as defined in claim 1, wherein said resistance wire is formed in a vortex shape.

* * * * *